United States Patent [19]

Heuscher

[11] Patent Number: 5,262,946
[45] Date of Patent: Nov. 16, 1993

[54] DYNAMIC VOLUME SCANNING FOR CT SCANNERS

[75] Inventor: Dominic J. Heuscher, Aurora, Ohio

[73] Assignee: Picker International, Inc., Highland Hts., Ohio

[21] Appl. No.: 567,300

[22] Filed: Aug. 14, 1990

Related U.S. Application Data

[63] Continuation-in-part of Ser. No. 260,403, Oct. 20, 1988, Pat. No. 4,965,726, and a continuation-in-part of Ser. No. 438,687, Nov. 17, 1989.

[51] Int. Cl.⁵ .............................................. G06F 15/00
[52] U.S. Cl. ........................ 364/413.18; 364/413.17; 364/413.19
[58] Field of Search ....................... 364/413.17, 413.18, 364/413.19

[56] References Cited

U.S. PATENT DOCUMENTS

| | | | |
|---|---|---|---|
| 3,432,657 | 3/1969 | Slavin | 250/53 |
| 4,093,859 | 6/1978 | Davis et al. | 250/445 |
| 4,293,912 | 10/1981 | Walters | 364/414 |
| 4,442,489 | 4/1984 | Wagner | 364/414 |
| 4,630,202 | 12/1986 | Mori | 364/414 |
| 4,789,929 | 12/1988 | Nishimura et al. | 364/413 |
| 4,868,747 | 9/1989 | Mori et al. | 364/413 |

FOREIGN PATENT DOCUMENTS

0365301A1 of 0000 European Pat. Off.
0383232A3 of 0000 European Pat. Off.
0426464A3 of 0000 European Pat. Off.

OTHER PUBLICATIONS

Image Reconstruction by Parametric Cubic Convolution Stephen K. Park; Computer Vision, Graphics and Image Processing 23, 258-272.
Evaluation of a Prototype Dual-Energy Computed Tomographic Apparatus I Phantom Studies; Kalender, et al.; Med. Phys. 13(3) May/Jun. 1986 p. 334.
Evaluation of a Prototype Dual-Energy Computed Tomographic Apparatus II Determination of Vertebral Bone Mineral Content; Vetter, et al.; Med. Phys. 13(3) May/Jun. 1986; p. 340.
Generalized Image Combinations in Dual KVP Digital Radiography Kalender, et al.; Med. Phys. 8(5) Sep.-/Oct. 1981 p. 659.
Power-injected CT Contrast Opacifies Vascular Spaces Sam D. Lane, M.D.; Diagnostic Imaging, Nov., 1988.
"World's Fastest CT" advertising brochure of Picker International, Inc.

*Primary Examiner*—Roy N. Envall, Jr.
*Assistant Examiner*—Ari M. Bai
*Attorney, Agent, or Firm*—Fay, Sharpe, Beall, Fagan, Minnich & McKee

[57] ABSTRACT

The radiation source (22) rotates around a patient on a patient couch (30) as the couch is advanced through an examination region (14). Radiation detectors (24) detect radiation that has passed through the patient along rays of a plurality of fan shaped views. Each view is identifiable by its angular position around the examination region and its longitudinal position in the spiral and each ray is identifiable by its angular position in the fan. An interpolator (46) interpolates views collected over more than two revolutions of spiral path using an interpolation function (FIGS. 1A-1D). A set of interpolated views is reconstructed (54) into a series of image representations representing parallel planar slices through the imaged volume. In some reconstructions, particularly reconstructions in which a 180° based reconstruction algorithm is used or the energy of the x-ray beam is varied, the filter function is varied from ray to ray within each view. A projection filter can also be varied from view to view in order to emphasize structures along various axes of a subject. A cardiac or other physiological condition monitor (90) monitors for movement of the subject so that one or more of the rotational speed of the x-ray source, movement of the patient table, energy of the x-ray beam, or filter function can be varied accordingly.

43 Claims, 12 Drawing Sheets

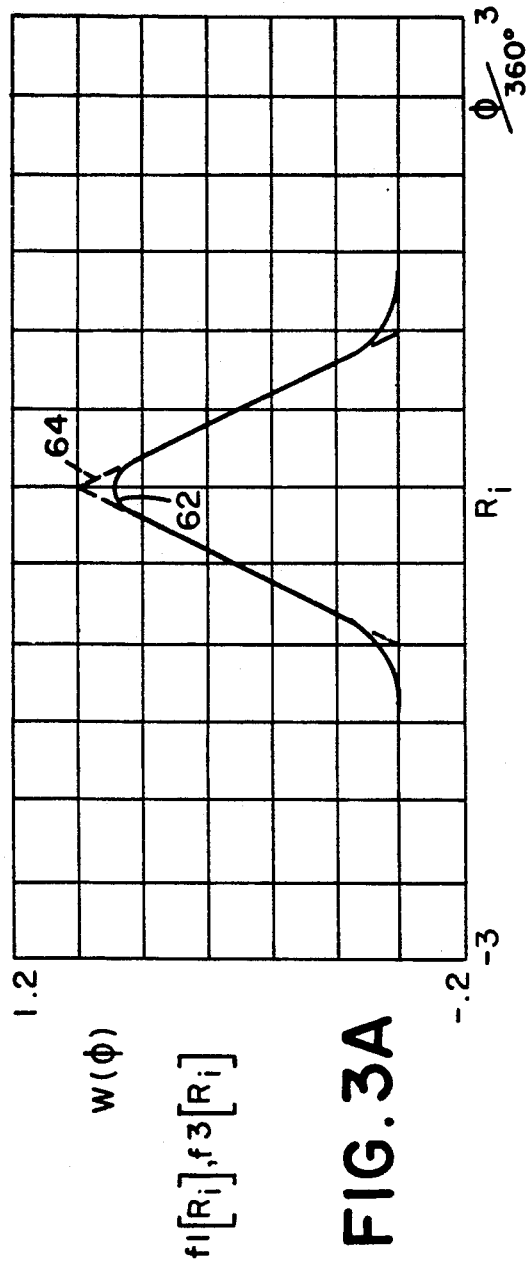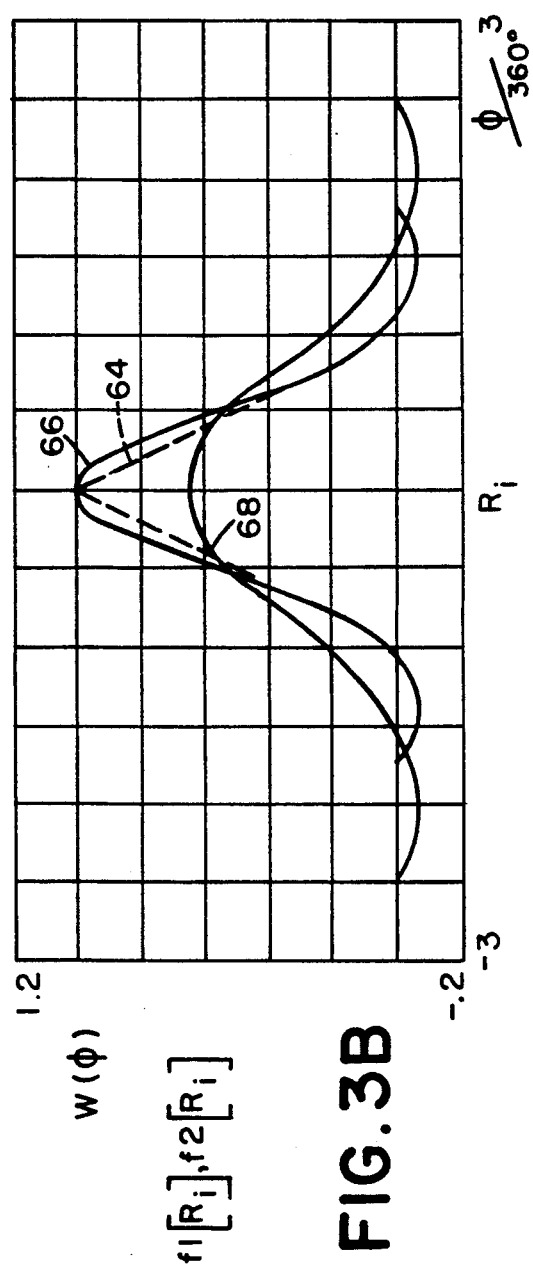

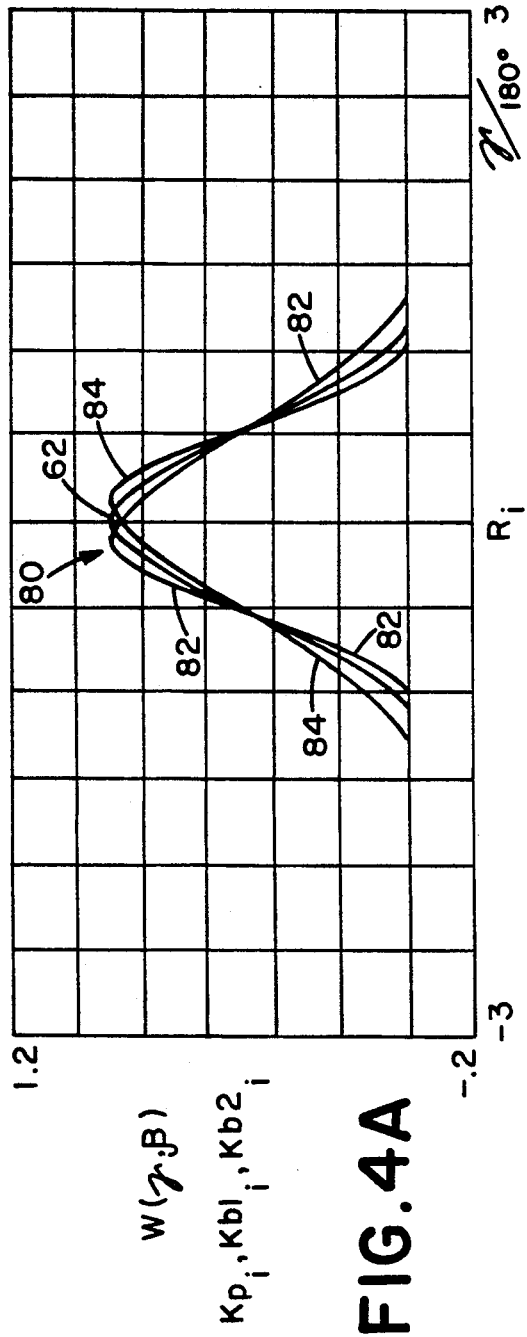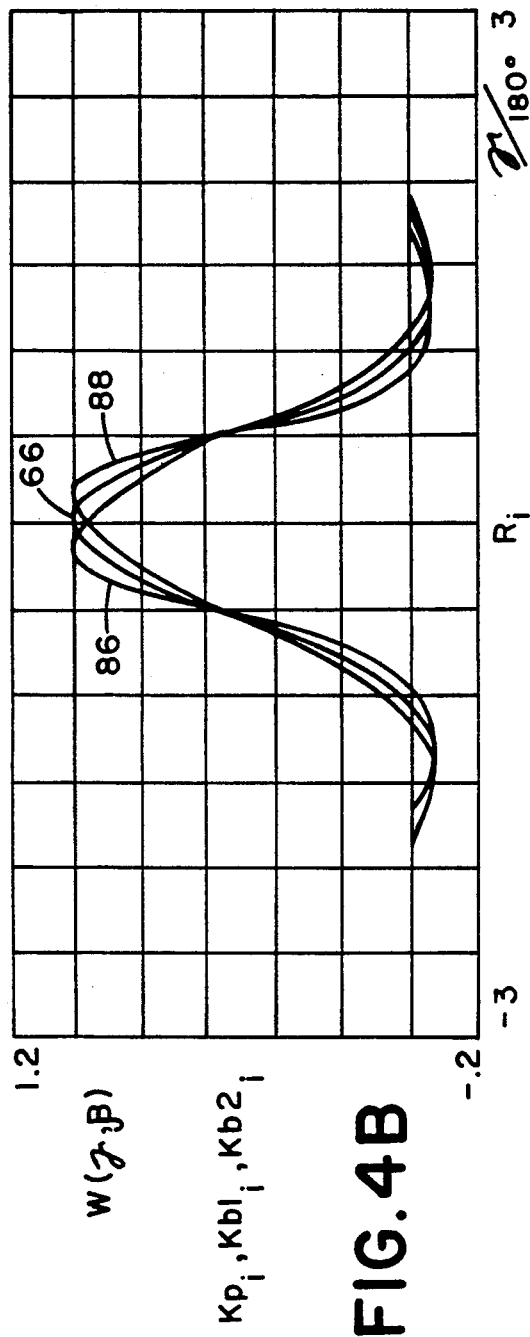

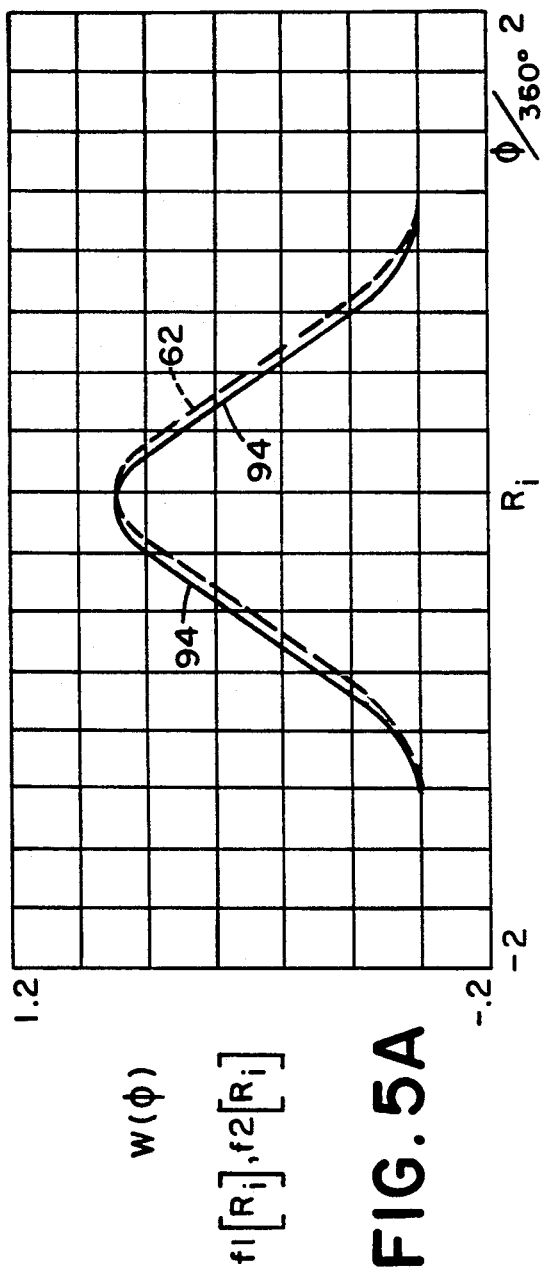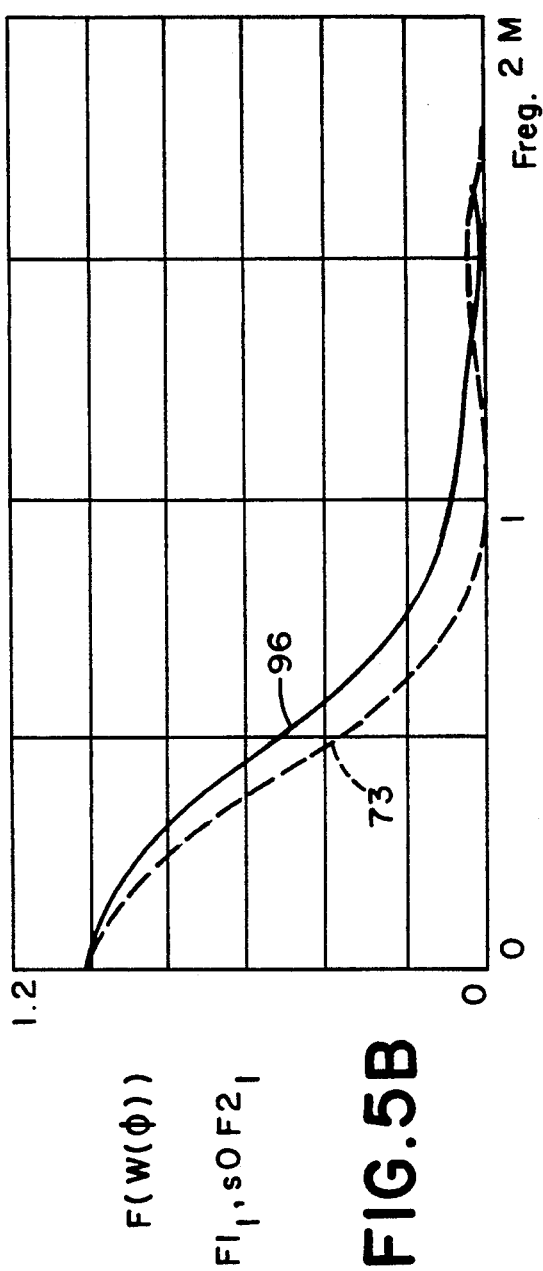

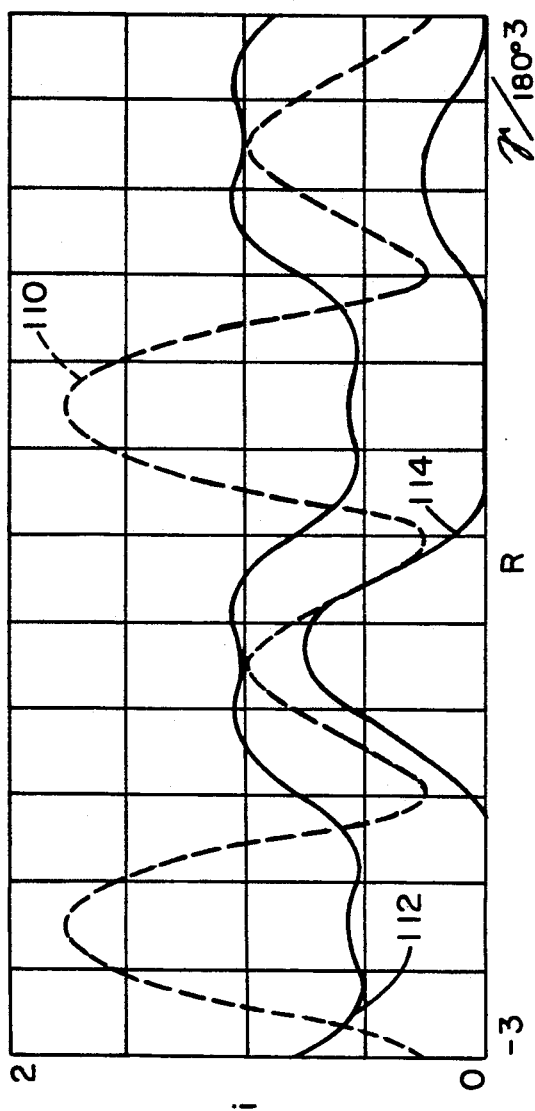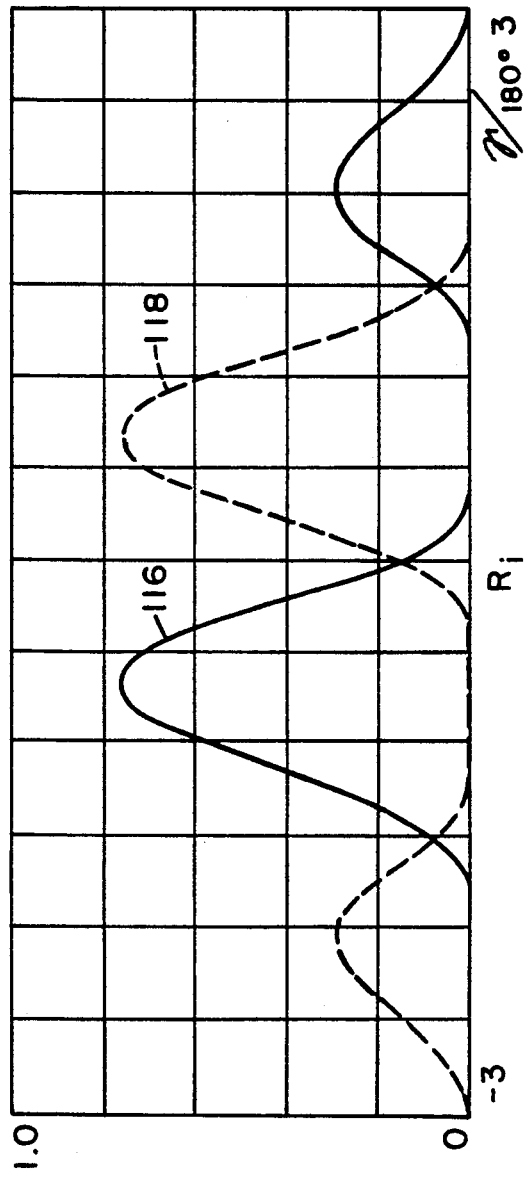

DYNAMIC VOLUME SCANNING FOR CT SCANNERS

This application is a continuation-in-part of application Ser. No. 260,403, filed Oct. 20, 1988, now U.S. Pat. No. 4,965,726, and U.S. application Ser. No. 438,687, filed Nov. 17, 1989.

BACKGROUND OF THE INVENTION

The present invention relates to the art of medical diagnostic imaging. It finds particular application in conjunction with spiral volume imaging with CT scanners and will be described with particular reference thereto. However, it is to be appreciated that the invention will also find application in conjunction with other types of volume imaging, with multiple single slice images, continuous rotating x-ray source images, gated imaging, and the like.

In spiral or helical scanning, the x-ray source or tube rotates continuously as the patient support table moves at a constant, linear velocity. In this manner, the collected data effectively represents a helical path of constant pitch through the patient. Conventionally, the data is stored and handled as a series of parallel planes, transverse to the longitudinal axis of the patient, or more specifically, as a three dimensional rectangular matrix of memory cells. See for example U.S. Pat. No. 3,432,657 to Slavin.

In order to fit the spiral collected data into a conventional three dimensional rectangular matrix, a series of parallel planes are defined through the spiral collected data, with a one plane per spiral revolution, e.g. at each 0° of source rotation. During the data collection period, a series of views or fans of data are collected at preselected angular increments around the patient. Potentially, one view per plane, by convention the 0° or 12 o'clock view, falls squarely in the plane requiring no averaging or weighting. For each remaining view of the plane, there is a pair of corresponding views or data fans, one from the revolution preceding the plane and the other from the revolution following the plane. These views are averaged or weighted in accordance with their relative distance from the plane. In this manner, a full set of weighted views is created to perform a conventional 360° CT reconstruction algorithm. See U.S. Pat. No. 4,630,202 issued December 1986 to Mori and U.S. Pat. No. 4,789,929 issued December 1988 to Nishimura, et al.

One of the problems with the spiral scanning techniques is that excessive partial volume artifacts were caused in certain applications. Another problem is that the linear interpolation or weighting is only applicable to 360° based revolution reconstruction techniques, not 180° plus fan reconstruction algorithms. See U.S. Pat. No. 4,293,912 issued October 1981 to Walters.

Another problem with the linear interpolation technique is that it introduces errors in fourth generation scanners using source fan reconstruction. In a third generation scanner in which the x-ray source and an arc of detectors rotate together about the slice, each data fan or view is collected instantaneously in a plane parallel to the artificially defined transverse slices. In a fourth generation scanner, there is a parallel ring of stationary detectors surrounding the patient. With source fan reconstruction, each detector is sampled at monitored, time displaced intervals generating a view or fan of data as the source rotates behind the examination region. Because the patient moves longitudinally between the first and last data sampling of the view or data fan, the views are warped or canted along the spiral path. The linear interpolation scheme which assumes that the views lie parallel to the artificially defined planes introduces errors.

Another problem with the linear interpolation technique is that it is particularly sensitive to variations in the x-ray rotation speed, the velocity with which the patient is moved, and fluctuations in the output of the x-ray tube.

Continuous rotation of the x-ray source with a stationary patient has been utilized for gated scanning. See for example U.S. Pat. No. 4,868,748 issued September 1989 to Mori. In this technique, the patient remains stationary and the x-ray tube continuous to rotate in the same plane of the patient. In response to the R-wave of the patient's cardiac cycle, the x-ray tube or its shutter is gated on to collect a view of data. In this manner, data is collected over a plurality of cardiac cycles for constructing a stop-action slice through the patient's heart. Of course, this technique is not amenable to spiral volume imaging.

Another prior art CT scanner imaging technique includes the generation of two reconstructed images through the same slice but with different energies. The two different energy -images could be collected concurrently by pulsing the x-ray tube alternately at high and low energy levels to collect the high and low energy views alternately. See "Generalized Image Combinations in Dual KVP Digital Radiography", Lehmann, et al., Med. Phys. 8(5), Sept./Oct. 1981. Alternately, the two images could be collected sequentially, i.e. all of the views of the low energy image followed by all of the views of the high energy image. See "Evaluation of Prototype Dual-Energy Computed Tomographic Apparatus, I Phantom Studies", Calendar, et al., Med. Phys. 13(3) May/June 1986 and "Evaluation of Prototype Dual Energy Computed Tomographic Apparatus II Determination of Vertebral Bone Mineral Content", Vetter, Med. Phys. 13(3) May/June 1986. However, each of these techniques required two rotations per slice, one rotation to collect the low energy image data and one rotation to collect the high energy image data or one rotation to collect half the low energy and half the high energy image data and a second rotation to collect the other half of the low energy and the other half of the high energy image data. Because two revolutions per image set are required, the prior art dual energy imaging techniques are not suited to linear weighted helical scanning.

In accordance with the present invention, a new and improved imaging technique is provided.

SUMMARY OF THE INVENTION

In accordance with a first aspect of the present invention, a helical or spiraling image technique is provided in which an arbitrary interpolation function interpolates corresponding data fans or views from more than two spirals or revolutions.

In accordance with another aspect of the present invention, an interpolation function based on ray angle within the data fan as well as the data fan angle is provided. This enables 180° based reconstruction algorithms to be utilized.

In accordance with another aspect of the present invention, a 180° image reconstruction algorithm is utilized in conjunction with spiral scanning.

In accordance with another aspect of the present invention, the frequency content of each projection or view is varied to provide a dynamic bandwidth capability. For example, projections around zero degrees are filtered the least and those near plus and minus 90° are most highly filtered. This reduces the effective time interval for moving structures. This also biases the reconstruction for movement to planes perpendicular to the zero degree position and can be better imaged in a sagittal or coronal plane.

In accordance with another aspect of the present invention, rotation of the x-ray tube and movement of the table are synchronized such that variations in one cause a corresponding variation in the other. Analogously, x-ray tube operating conditions, such as tube current can be synchronized with the gantry and table movement.

Analogously, in accordance with another aspect of the present invention, the rotation of the gantry is synchronized with physiological movement, e.g. the R-wave of the patient's ECG. In this manner, the gantry rotation can be varied such that the same structures are in the same position for each rotation. Table motion can still be synchronized to match the rotational variations such that a helical scan can still be obtained.

In accordance with another aspect of the present invention, the x-ray exposure can be varied in accordance with the dimensions of the subject for more consistent noise statistics along the wider and narrower cross section dimensions of the patient. Because the patient cross section stays in the same orientation, the x-ray exposure is advantageously varied in accordance with angular position of the gantry. The x-ray tube kV, the filtration, or the tube current can be varied to achieve the exposure variations.

In accordance with another aspect of the present invention, the beam quality of the x-ray output is varied between two limits to create a dynamic beam quality reconstruction to maximize tissue contrast while reducing beam hardening artifacts.

In accordance with another aspect of the present invention, the x-ray beam quality is cyclically varied during helical scanning. In accordance with another more limited aspect of this invention, the high and low kV scans are collected in alternating 180° scan sectors separated by 90° transition intervals. In accordance with another more limited aspect of the present invention, a segmented detector array having a plurality of detectors in the axial direction is utilized such that the axially displaced sets of detectors collect high and low energy scan data through the same tissue.

In accordance with another aspect of the present invention, a detector array having a plurality of detectors in the axial direction is utilized to collect data. The detectors may collect two or more interleaved spirals of data for a more dense data sampling. Alternately, the patient table may move at a higher velocity yet achieve the same sampling density in the axial direction.

One advantage of the present invention is that it provides for faster volume scanning.

Another advantage of the present invention is that it facilitates dual energy volumetric scanning.

Another advantage of the present invention is that it matches the scanning technique with physiological conditions of the patient.

Another advantage is that the motion effects can be minimized.

Another advantage is the longitudinal image quality is improved and partial volume effects are minimized.

Still further advantages of the present invention will become apparent to those of ordinary skill in the art upon reading and understanding the following detailed description.

BRIEF DESCRIPTION OF THE DRAWINGS

The present invention may take form in various components and arrangements of components and in various steps and arrangements of steps. The drawings are only for purposes of illustrating a preferred embodiment and are not to be construed as limiting the invention.

FIGS. 4A and 4B are illustrative of interpolation or weighting functions for 180° based reconstruction algorithms;

FIGS. 5A-5D are illustrative of compensations for gantry rotation and table speed variations, particularly variations in weighting functions for effecting the correction;

FIGS. 6A-6C are illustrative of x-ray current and kV fluctuations and corresponding weighting functions for dual kV imaging techniques;

DETAILED DESCRIPTION OF THE PREFERRED EMBODIMENTS

Figure 1:
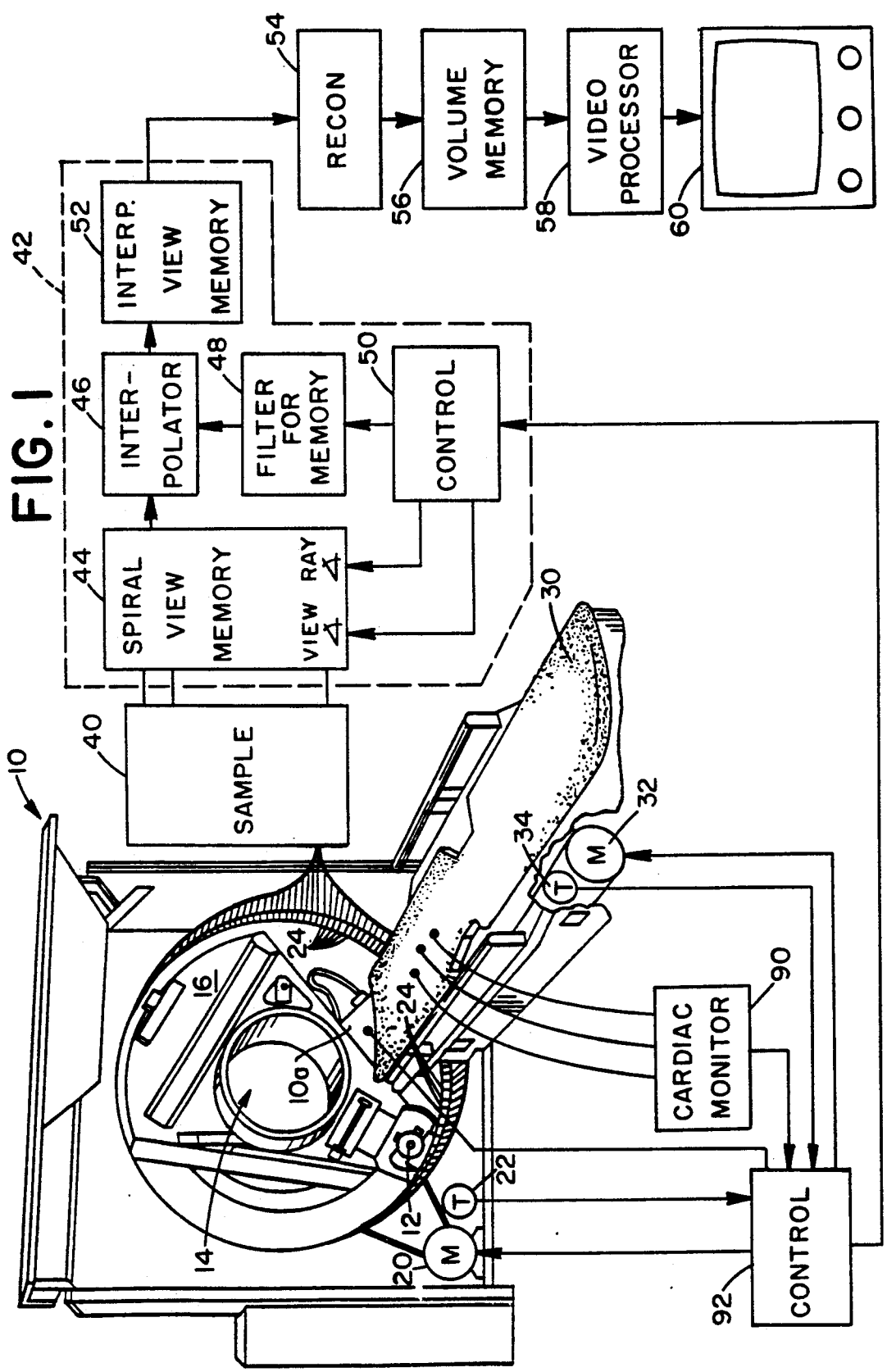
FIG. 1 is a diagrammatic illustration of a CT scanner in accordance with the present invention.

With reference to FIG. 1, a CT scanner 10 includes a radiation source 12, such as an x-ray tube, for projecting a fan beam of radiation through an examination region 14. The x-ray tube is mounted on a rotatable gantry 16 to rotate the fan beam of radiation around the scanned circle. A collimator and shutter means 18 collimates the beam of radiation to one or more narrow planar beams and selectively gates the beam on and off. The beam may be also gated on and off electronically at the x-ray tube. A motor 20 provides motive power for rotating the gantry 16 continuously around the examination region. A rotational position encoder 22 is connected with the motor and the gantry to measure the rotational position of the gantry.

Figure 2:
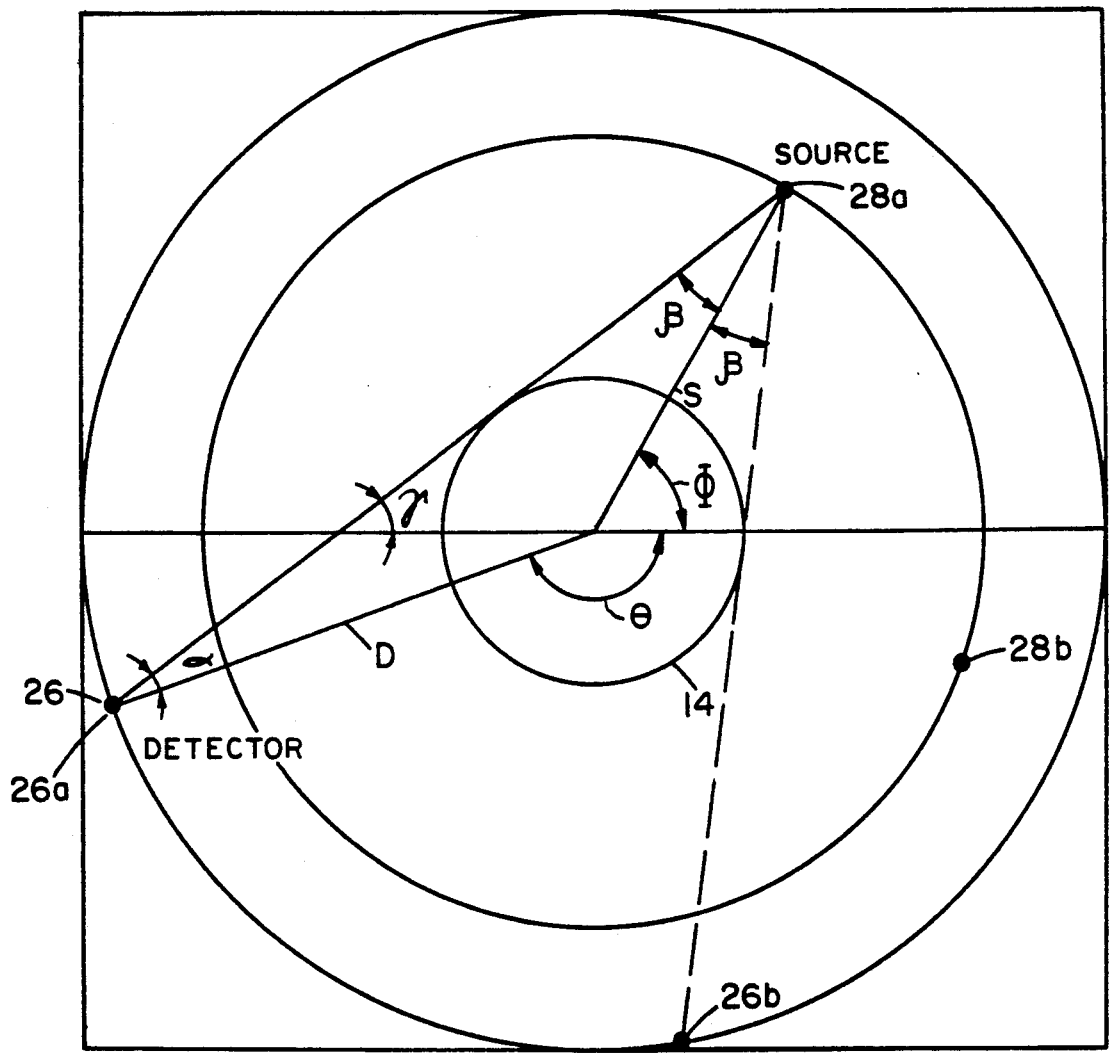
FIG. 2 illustrates the geometry of a CT scanner.

In the illustrated fourth generation CT scanner, a ring of radiation detectors 24 are mounted peripherally around the examination region. For mechanical and mathematical convenience, the detectors 24 are stationarily mounted around the rotating gantry in the same plane as the x-ray tube. With reference to FIG. 2, an arc of detectors are sampled 12 rotates in back of the examination region 14 to generate views or fan data sets. To generate detector fans, an exemplary detector 26 at an angular position $\theta$ is first sampled when the radiation source is at a location 28a tangent to one side of the examination region 14 and monitored incrementally until the radiation source reaches a point 28b in a line from the detector tangential to the other side of the examination region. For a source fan geometry, each of the detectors between detectors 26a and 26b are sampled concurrently to generate a source fan view or data set. The collected source fan data set can be identified by the angular position $\phi$ of its apex around the examination region. Each ray of data between the source and one of the detectors is described by an angle $\beta$. Each ray of the source fan also is identifiable by its angle gamma ($\gamma$) relative to the common axis. The source is disposed a radius S from the center of the examination region and the ring of detectors 24 is disposed a radius D from the center of the examination region. In a third generation scanner in which the invention is equally applicable, a single arc of detectors between detectors 28a and 28b are mounted to the gantry 16 for rotation with the source. A third generation source fan geometry is described mathematically the same.

With reference again to FIG. 1, a patient couch 30 supports a subject, particularly a human patient, in a reclined position. A means such as a motor 32 is provided for advancing the patient supporting surface of the couch through the examination region at a selectable velocity. An encoder 34 is connected with the motor 32, the moveable patient supporting portion 30, and the drive mechanism therebetween for monitoring the actual position of the patient supporting surface as it moves the patient through the scan circle 14.

A sampling means 40 samples the views or data sets corresponding to each angular position around the examination region 14 for each of a multiplicity of x-ray source rotations. A view processor 42 converts the spiral sampled views into a plurality of image representations corresponding to parallel planes. The view processor includes a view memory 44 in which the view data stored and addressable by a combination of the rotation number, view angle, and ray angle within the view. The view processor 42 further includes a filter or interpolation means 46 for interpolating the spiral data in the spiral view memory 44 into parallel slice data. The interpolation means 46 operates on a plurality of views of corresponding view angle with a filter or interpolation function supplied by a filter function memory 48.

A control means 50 indexes the view angle to each of the view angles in a complete set of views, e.g. the views disposed at regular increments 360° around the examination region. A plurality of views corresponding to each individual view angle are transferred to the interpolation means to be filtered into an interpolated view. Each interpolated view is stored in an interpolated view memory means 52 until a full set of views for reconstruction is generated. Thereafter, an image reconstruction means 54 uses a conventional filtered backprojection or other reconstruction algorithm to reconstruct each of a plurality of slices and store the resultant slices in a volume data memory means 56. The volume data memory means stores a rectangular pixel array corresponding to each of a plurality of slices, the slices being spaced a distance commensurate with the resolution of the pixels in each slice. In this manner, the data in the volume data memory means can be conceptualized as a rectangular data volume. A volume memory access means and video processor 58 accesses selected memory cells of the volume data memory means 56 to withdraw radiation attenuation or absorption information representative of a corresponding volume or surface through the patient and converts such information into a video signal for display on a display means 60 such as a video monitor.

With reference to FIG. 3A, the interpolation function memory means stores a plurality of filter or interpolation functions. FIG. 3A compares a modified linear weighting function 62 with a prior art linear weighting 64. The modified linear weighting function $W(\phi)=0$ for $|R|>1.5$ with an average width of 1.1, where $\phi=R\cdot 360°$. $W(\phi)$ and its first derivative are both continuous as is represented by the rounding adjacent $R=0$ and $R=\pm 1$. The rotational index R is the sum of the integral rotation index m and the fractional rotation index r. Moreover, the weighting function has unity weighting, i.e.

$$\sum_m W(\phi_m) = 1, \text{ for } 0 < r < 1 \tag{1}$$

where $$\phi_m = (r+m)360°$$

and the first moments are equal to zero, i.e.

$$\sum_m (r+m)\cdot W(\phi_m) = 0, \text{ for } 0 < r < 1. \tag{2}$$

In FIG. 3B, a cubic weighting function 66 which spans four contiguous rotations is compared with the conventional linear interpolation 64. In the cubic interpolation, $$W(\phi)=0, \text{ for } |R|>2 \tag{3}$$

with an average width $\approx 1.1$. $W(\phi)$ and its first derivative are again continuous and the conditions of Equations (1) and (2) are also valid. Analogously, a cubic weighting of the form 68 may also be utilized where $$W(\phi)=0, \text{ for } |R|>3 \tag{4}$$

and with a width (at half height) equal to 1.6 rotations.

Figure 3C:
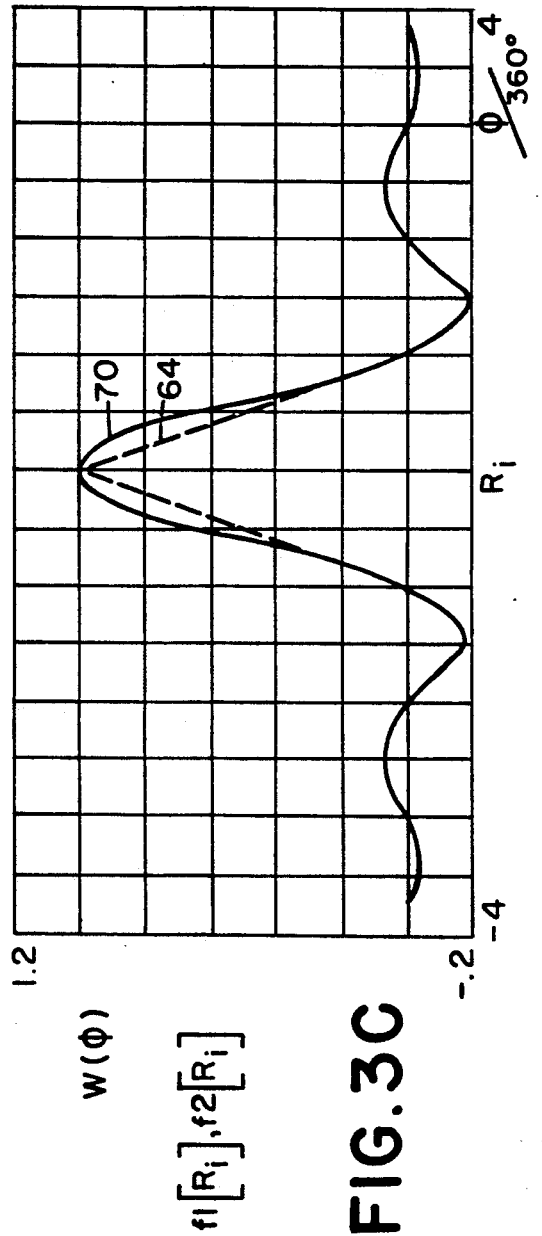
FIGS. 3A-3P are illustrative of different weighting functions for weighting among the more than two helical rotations.

FIG. 3C compares the conventional linear weighting 64 with a 7-lobe helical weighting function 70 where:

$$W(\phi)=0, \text{ for } |R|>4 \tag{5}$$

Again, the function and its first derivative are continuous and the conditions of Equations (1) and (2) are met.

Figure 3D:
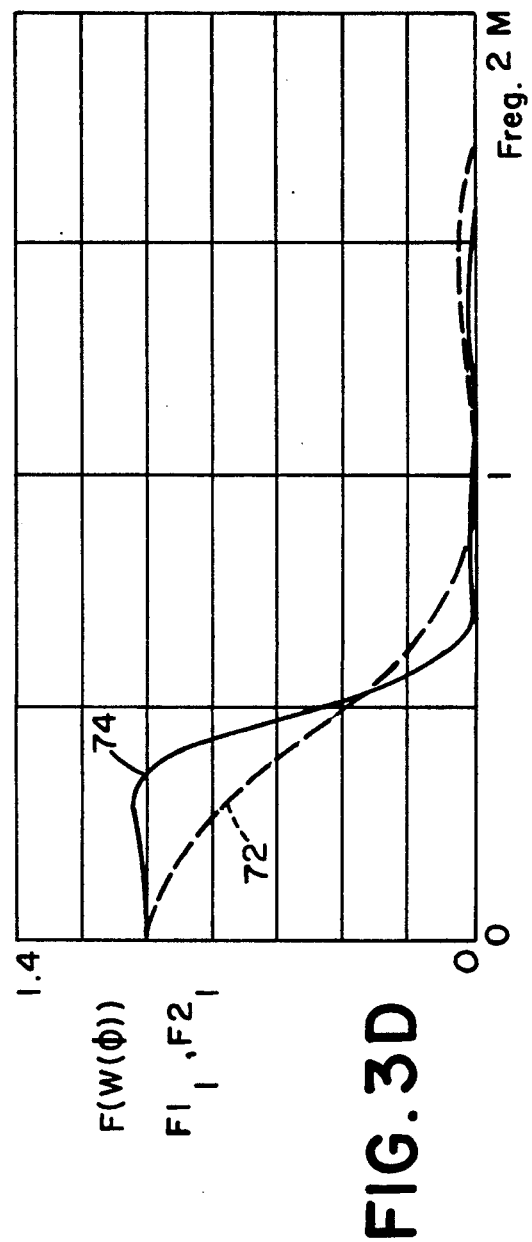

With reference to FIG. 3D, the conventional linear weighting of curve 64 has a relatively limited frequency response 72 along the z-axis. By distinction, the 7-lobed helical weighting function 70 has a much crisper frequency response 74 in the z direction. Note that the frequency response of the 7-lobed helical weighting 74 is relatively flat and drops off relatively quickly which eliminates the smoothing heretofore required with the linear weighting function.

It should be noted that the revolution number or longitudinal position R in FIGS. 3A–3D is not measured digitally. That is, if the detector crosses the even integer values $R=0$, $\pm 1$, $\pm 2$, etc., at 0°, then at 90°, the R position is $-0.75$, $+0.25$, $+1.25$, etc.

In accordance with another embodiment of the present invention, the reconstruction means 54 uses a reconstruction algorithm based on views spanning 180° plus the fan angle, such as the algorithm illustrated in U.S. Pat. No. 4,293,912 issued October 1981 to Walters. To utilize the 180° redundancy in the data most effectively with interpolation functions of the shapes described above but of half the extent, the interpolating filter from filter memory 48 is redefined on a 180° basis. Specifically, the linear weighting 64 would result in a warped rather than a planar image representation.

With reference to FIG. 4A, a preferred technique for using 180° basis reconstruction techniques is to use a weighting function based on both the view angle and the angle of each individual ray within the view. Curve set 80 includes the modified linear function 62 for the center or zero ray of the view or fan. Curve 82 illustrates the modified weighting function shifted for the ray at one extreme of the fan and curve 84 illustrates the modified weighting function shifted for the ray at the opposite extreme of the fan. For each ray in between, the extreme and central rays, the weighting function is shifted a fraction of the illustrated difference. Each weighting curve and its first derivative are still continuous but now meet the conditions of Equations (6) and (7) below. The sum of the weighting functions for rays which are 180° opposite to each other is equal to one.

$$\sum_m W(\gamma_m, (-1)^m \beta) = 1, \text{ for } \gamma_m = (r + m) \, 180° \quad (6)$$

Also, the first moments are equal to zero, i.e.

$$\sum_m \left( r + m + \frac{(-1)^m \beta}{180} \right) \cdot W(\gamma_m, (-1)^m \beta) = 0. \quad (7)$$

For projection data organized in the form of source fans $$V_S(\Phi + n \cdot 360°, \beta),$$

the longitudinal interpolation generates:

$$D_{180}(\phi, \beta) = \sum_n W_S(\phi + n \cdot 360°, \beta) \cdot V_S(\phi + n \cdot 360°, \beta) \quad (8a)$$

where:

$$W_S(\phi + n \cdot 360°, \beta) = W(\gamma + \beta, \beta)$$

and $W_s (\gamma, \beta)$ is the weighting function that satisfies conditions (6) and (7).
and
$\phi = 0°$ to 360°.
$\beta_o = $ fan angle defining the scan circle.

The resulting 360° of projection data $D_{180} (\phi, \beta)$ no longer has unity weighting, but instead has an average weighting spanning 180°. This data can be reconstructed using standard convolution backprojection of $D_{180}(\Phi, \beta)$ for $\phi = 0°$ to 360°. For projection data organized as detector fans $V_D(\theta + n \cdot 360°, \alpha)$, the longitudinal interpolation generates:

$$D_{180}(\theta, \alpha) = \sum_n W_D(\theta + n \cdot 360°, \alpha) \cdot V_D(\theta + n \cdot 360°, \alpha) \quad (8b)$$

where $W_D (\theta + n \cdot 360°, \alpha)$ is obtained by remapping $W_s (\theta + n \cdot 360°, \beta)$ from source fan format to detector fan format. Again, this data can be reconstructed using standard convolution backprojection of $D_{180} (\theta, \alpha)$ for $\theta = 0°$ to 360°.

Analogously, the weighting function $W_{180}(\gamma, \beta)$ for the cubic weighting function of curve 66 of FIG. 3B can be made ray dependent as illustrated in FIG. 4B. Specifically, cubic weighting function 66 is used for the central ray. For the ray at one extreme, the weighting function is distorted as illustrated by curve 86 and for the ray of the other extreme of the fan, the weighting curve is distorted as illustrated at 88. In the illustrated embodiment, the extreme rays of curves 86 and 88 are for $\beta = \pm 23°$.

Looking to another aspect of the invention, the reconstruction filter function 54 may also be varied on a view angle and ray angle basis to vary the frequency content of the projections. For example, the torso of a human subject is generally an oval that is significantly wider than it is high. The path length through the patient for some rays is significantly longer than for others. In accordance with another aspect of the present invention, the cross sectional size and shape of the patient are measured to determine the relative path length for each view and ray angle. Alternately, the ray lengths for one or more standardized cross sections can be calculated and stored and the most nearly accurate cross section selected. The bandwidth of the filter function is adjusted generally in proportion to the ray length through the subject. In an oval human torso, projections around 0° or straight over head are filtered the least and those near ±90° are the most highly filtered. Analogous advantages can be obtained by varying the filter function with the view angle only.

A cardiac or other cyclic event monitor 90 and the encoder 22 are interconnected with a rotation control means 92. The rotation control means controls the motor 20 such that the x-ray source 12 rotates synchronously with the normal cardiac cycle of the patient. More specifically to the preferred embodiment, the x-ray tube rotates once per cardiac cycle such that the x-ray source is at the same preselected angular orientation at the same preselected point in each cardiac cycle.

Synchronization of the movement of the source with cardiac and other patient movement is advantageously utilized in conjunction with the angle dependent filtering technique. By lightly filtering views with the heart in one preselected phase and more heavily filtering views taken when the heart is in another phase, blurring of cardiac and cardiac related motion is diminished. With appropriate filtering, a substantial freeze action of the heart may be obtained. Of course, movement of the source may be synchronized with other subject movement. In this manner, reconstruction is biased towards planes with the minimal filtering. When the minimal filtering is at 0° or straight above, imaging in the sagittal or coronal plane is enhanced and degrading motion is minimized.

This technique is also applicable to performing rapid scans to watch the advancement of a contrast agent injected into the patient. As an example of one specific implementation, the patient is moved in a first direction to create one helix of data and then moved in the other direction to create a second crossing helix in the opposite direction covering the same volume. This minimizes the delay between passes but does not provide time information for a given slice in equal intervals. In a second embodiment, a steep pitch helix is selected, for example, one which collects only about half the normal number of views. The patient may then be shifted back to the beginning and the other half of the views are collected along a second helix. This process may be repeated again and again to collect half data sets at close time displaced intervals. Image data may be reconstructed, combining time adjacent data sets into a complete data set to provide a series of time incremented volume images to watch the migration of the contrast agent through the patient, or other physiological changes. When the corresponding views are longitudinally taken in different passes, it is preferred that one of the longer longitudinal weighting functions be applied, such as the 7-lobe helical weighting of FIG. 3C. Note, the ends of each pass are processed with a shortened weighting function for imaging the end slices. For even faster scanning, this technique is advantageously utilized with a 180° basis reconstruction algorithm and weighting functions discussed above.

The control means 92 is also connected with the table moving means 32 such that movement of the patient is coordinated with rotation of the x-ray source. As the speed of rotation of the x-ray source and the velocity of table movement change, the relative weighting of the views is also altered. Note that a given helix can be maintained at proportionally higher source rotation and patient advancement rates but the radiation dose per view and sample intervals changes. These variations in speed can also produce a scanning path which is non-helical. Analogous problems arise when the rotational velocity of the x-ray source or the linear velocity of the patient table is not accurately controlled. For example, the mechanics of either of these movements whether through wear, power fluctuations, or the like may vary.

With reference to FIG. 5A, interpolation function 62 is recalculated to function 94 to account for a ±20% sinusoidal speed variation. Specifically:

$$\sum_m W_A(\phi_m) = 1, \text{ for } \phi_m = (r + m) \cdot 360 \tag{9}$$

$$\sum_m P(\phi_m) \cdot W_A(\phi_m) = 0, \tag{10}$$

where $P(\phi)$ is the table position relative to rotational angle $\phi$. Although this satisfies the requirement for planar reconstructions, FIG. 5B shows that the spatial resolution of curve 94 does not match the resolution 73 of curve 62. However, if the values of the weighting function $W(\phi)$ are remapped to $W(P(\phi))$, a constant spatial response can be maintained. This weighting is adjusted such that $$\sum_m W_A(P(\phi_m)) = 1, \text{ for } \phi_m = (r + m) \cdot 360 \tag{11}$$

$$\sum_m P(\phi_m) W_A(P(\phi_m)) = 0. \tag{12}$$

Figure 5C:
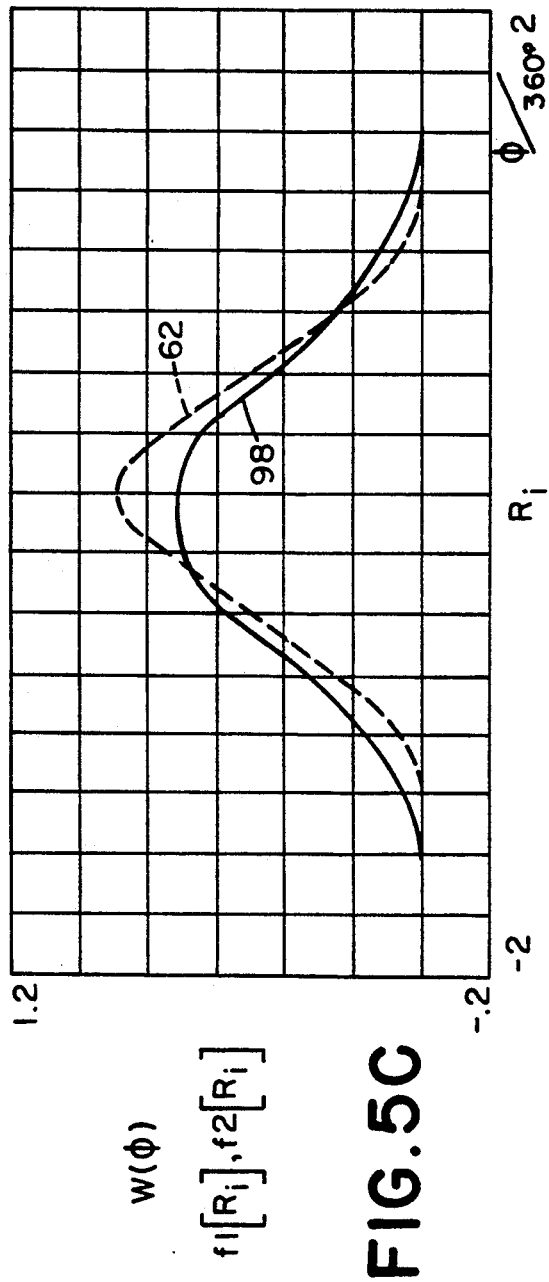
Figure 5D:
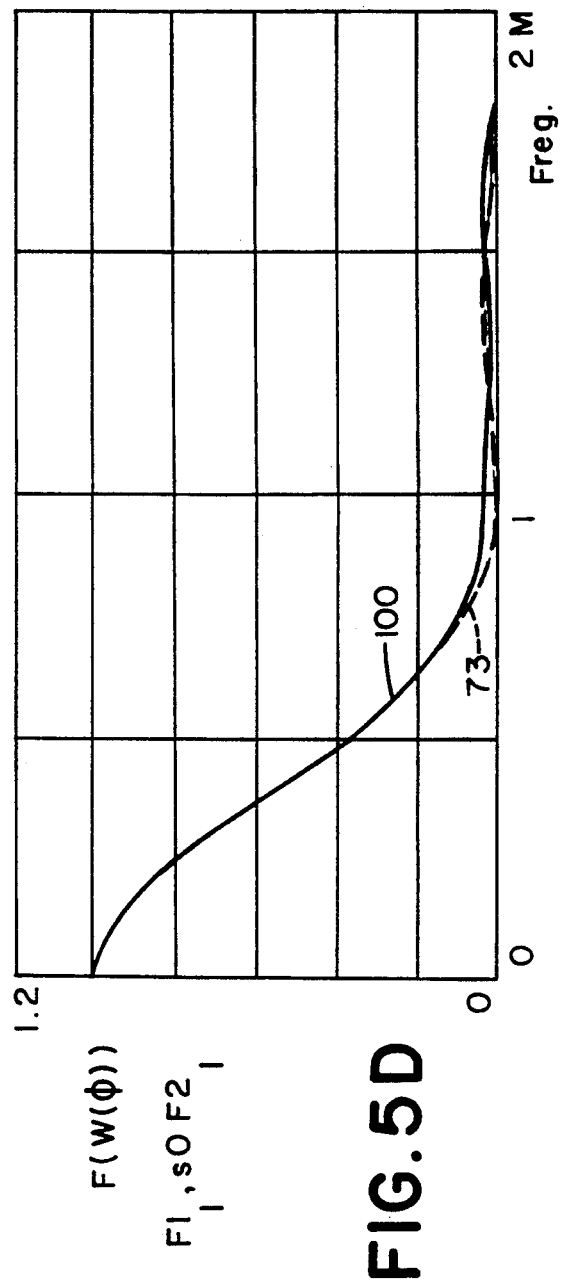

With the new weighting function 98, a spatial response 100 of FIG. 5C is substantially the same as the spatial response 73 of FIG. 5B. In this manner, the interpolation function is utilized to correct for fluctuations in the speeds of relative movement of the source and patient.

Another application is to adjust the exposure of a subject that does not have a circularly uniform attenuation. As indicated above, a human patient commonly has an oval cross section. The synchronization control means 92 further controls a power supply 104 for the x-ray tube 20. The power supply adjusts the x-ray tube current or voltage generally in proportion to the mean attenuation path through the patient for each angular position of the x-ray tube. By varying the exposure in this manner, the quantum noise statistics of the reconstructed volume can be made more uniform.

When the gantry rotation or table speed are varied disproportionately, the scan becomes non-helical. However, (as demonstrated above), a suitable reconstruction volume can still be attained. For higher attenuation projections, either the gantry rotation or the table movement is slowed to compensate for the higher quantum noise. Analogously, if the x-ray tube voltage, the filtration, or the x-ray tube current is varied, a helical scan can still be performed. Specifically, the voltage filtration and/or current are increased for higher attenuative projections. The synchronization of these parameters may be either predetermined based on previous estimates or may be determined by estimates from earlier projections or scans of the same volume.

As discussed above, the views may be grouped into a group spanning 360° for 180° based reconstructions. The energy level (kV) of the x-ray tube in another embodiment is varied or alternated between two levels. By continuously varying the kV with a prescribed high to low variation as shown in 112 of FIG. 6A, two weighting functions (116, 118) can be applied to the respective projections to produce two sets of 180° based projections, both of which correspond to the same imaging plane. The average kV value for each ray in each set corresponds to either the high kV level or low kV level. Exactly 1½ rotations are required for each cycle from high kV to low kV back to high kV. The x-ray current 110 is varied counter cyclically to maintain the noise in both the high and low kV projections while minimizing the total exposure. Curve 114 identifies the high kV weighting function, $W_{hi}(R \cdot 180, \beta) = W_{hi}(\gamma, \beta)$.

With reference to FIG. 6B, the weighting function applied by the interpolating means 46 shifts for the high and low kV portions. That is, curve 116 illustrates the preferred weighting function for the high kV or voltage projection rays whereas the curve 118 illustrates the weighting function used with the low energy rays. These ray projections are recombined into two separate 180° based sets or groups of projections. In the illustrated embodiment, the beam width corresponds to about three rings of the helix and a reconstructed image or slice is obtained for every one and a half rings of the helix.

Figure 6C:
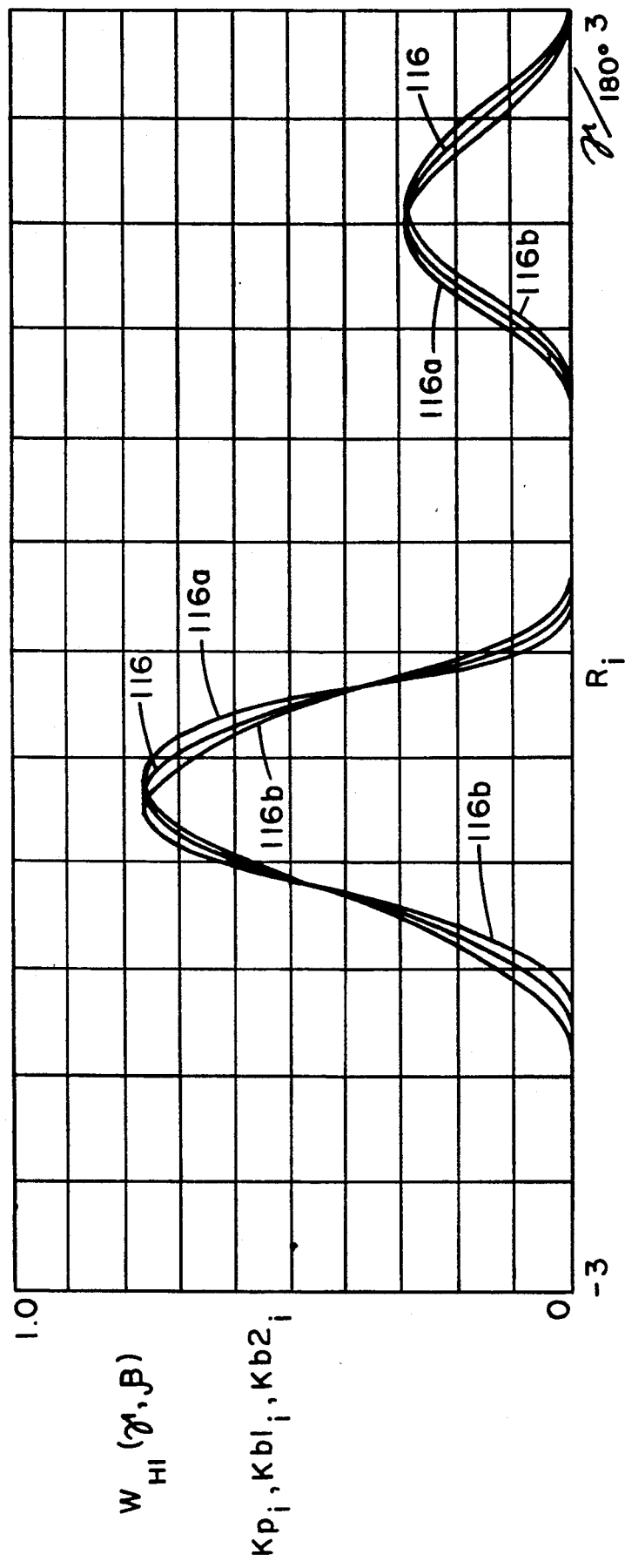

With reference to FIG. 6C, the variation in weighting values for the extremes of the fan $(\beta = +/- \beta_o)$ is illustrated for the high kV 180° based projection set. More specifically, weighting function curve 116 is shifted or swayed between curve 116a at one extreme ray of the fan and 116b at the other extreme ray of the fan. Analogous shifts are made for the weighting function 118 for the low kV projection set.

To increase the x-ray collection efficiency, a plurality of detectors are positioned adjacent to each other in the longitudinal direction. Positioning two detectors longitudinally enables the width of the radiation seen by each detector to be selectively adjusted at the detector. Analogously, three or more detectors can be disposed in longitudinal alignment. This enables data along three interleaved spirals to be collected concurrently. In one embodiment, the three spirals of data cover the same volume with a greater sampling density. This is particularly advantageous in the dual energy modes described above. Alternately, the speed of the patient table is tripled such that the three sets of detector collect data with the same sampling density but three times as fast.

Figure 7:
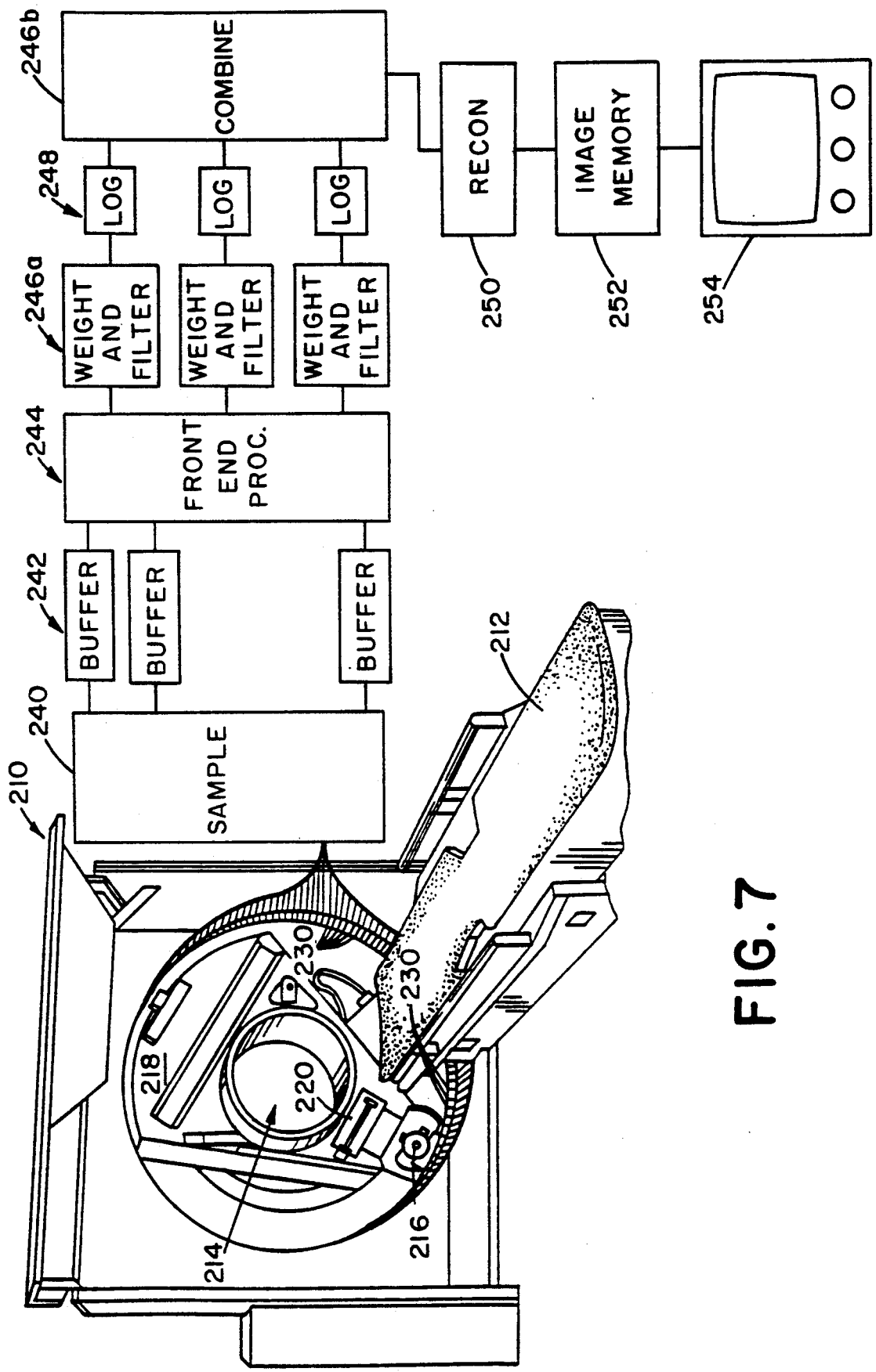
FIG. 7 is another diagrammatic illustration of a CT scanner in accordance with the present invention.

With reference to FIG. 7, a CT scanner 210 selectively images cross sectional slices of a region of a patient supported on a stationary patient couch 212 within a scan circle or patient aperture 214. In some applications, the patient couch is incremented to take a plurality of parallel slices. In another embodiment, the couch moves continuously such that the patient is scanned along helical paths. An x-ray tube 216 for emitting a fan-shaped beam of radiation toward and spanning the scan circle 214 is mounted to a rotatable gantry 218. Alternatively, a multispot x-ray tube may be utilized to increase the thickness of the fan beam or generate plural parallel beams.

Figure 8:
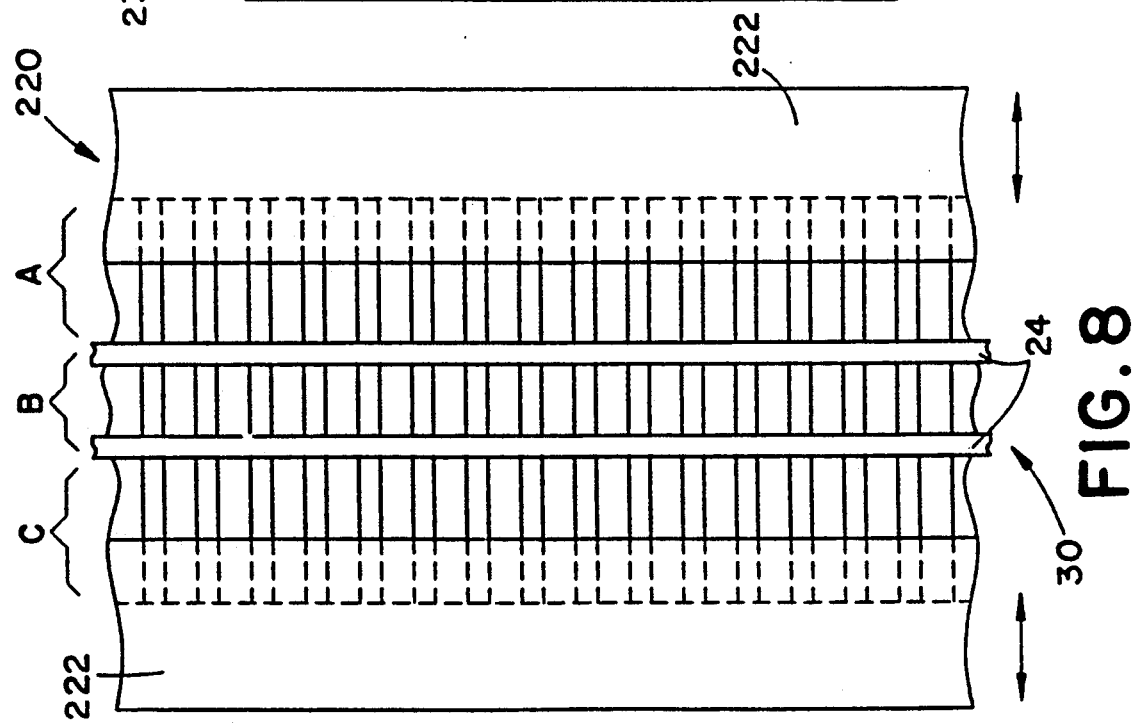
FIG. 8 illustrates a portion of collimators overlying a segmented detector array.

With reference to FIG. 8, a collimator 220 defines the dimensions of the x-ray beam(s), particularly its width to select the thicknesses of an individual slice or group of slices which are imaged. An outer continuously adjustable collimator 222 sets the overall width of the x-ray beam, i.e. the width of the outer slices. If the outer collimator is closed sufficiently, the outer slices may be eliminated and the center or inner slice(s) can be narrowed. If the halves of the outer collimator are moved independently, one of the outer slices may be eliminated and the other adjusted to a selected width, e.g. the width of the inner slice. An inner collimator 224 selectively narrows the radiation received by the center detectors, i.e. narrows the center or inner slice. In the preferred embodiment, the inner collimator has a fixed profile which is selectively moved into and out of the radiation beam. Optionally, the fixed collimator segments may have selectable profiles such that the center slice collimation is adjustable. Other mechanical slice thickness adjustment or selection devices for the inner and outer slices may, of course, be utilized.

A plurality of segmented detector array modules 230 receive radiation which has traversed the scan circle and provide output signals indicative of the intensity of received radiation. In the preferred embodiment, 128 detector modules each include three segments of 24 photodiodes to define three rings of 2,880 detectors per ring around the scan circle.

Figure 9:
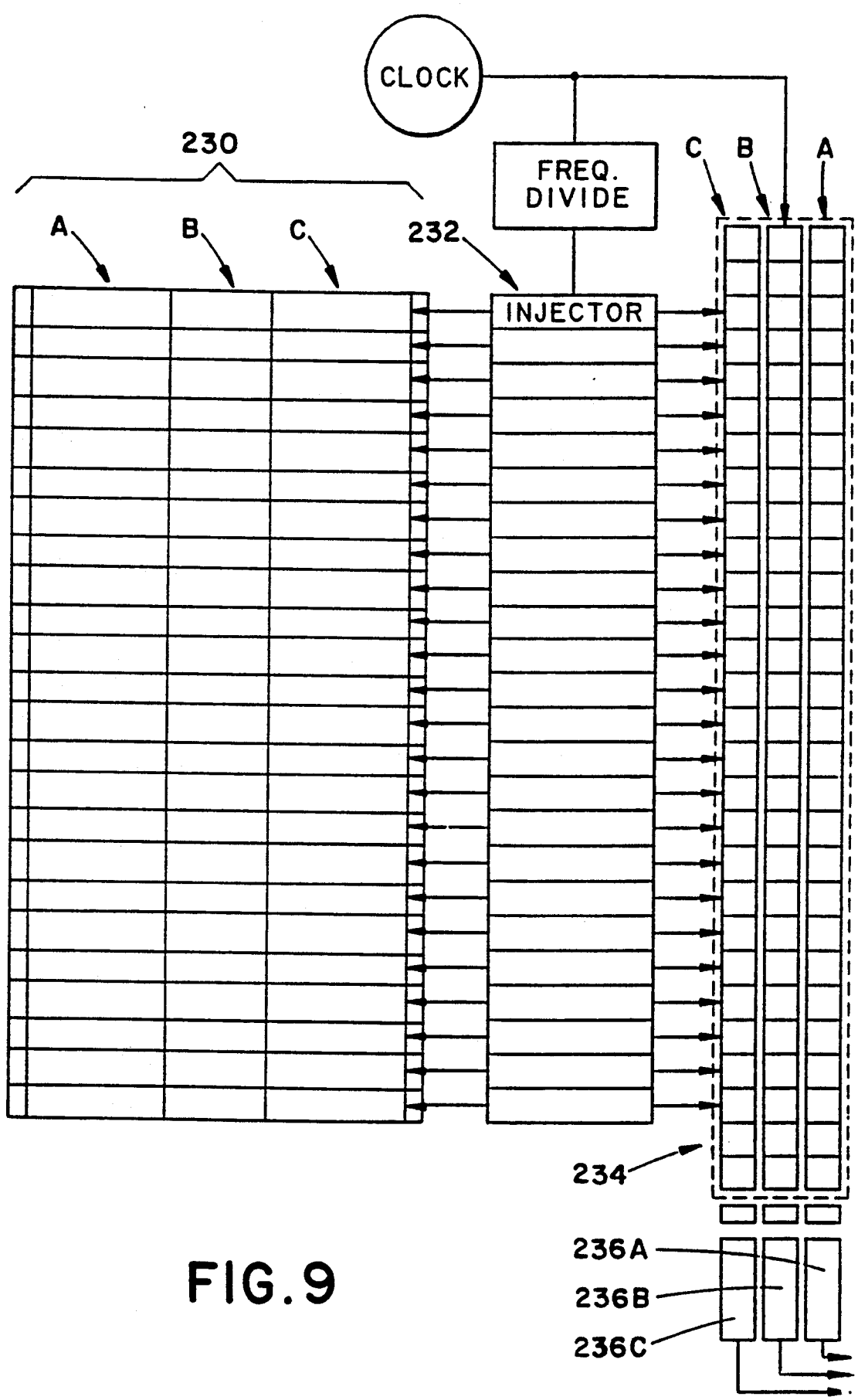
FIG. 9 illustrates a segmented photodiode array in combination with a CCD array; and, FIG. 10 is illustrative of a segmented diode array in combination with an FET array on a single substrate.

With particular reference to FIG. 9, each detector module includes three rows or segments A, B, C of 24 x-ray sensitive cells each. The cells of row A are labelled A1–A24, etc. Of course, other numbers of rows, such as five or more, may be provided and other numbers of radiation sensitive cells may be provided within each array without departing from the present invention. The center row or segment B preferably is narrower than the side segments A and C. This enables the center segments to have higher resolution or define a narrower slice. By selectively adjusting the collimator 220, the amount of radiation impinging on the outer segments A and C and the amount impinging on inner segments B are selectively adjustable. This enables the slice defined by the outer segments to be the same as the center segment, wider, or narrower. Within each segment, there are a plurality of different width detectors. In the preferred embodiment, wider detectors A1, A3, A5, ... A23, B1, B3, ... B23, C1, C3, ... C23 alternate with narrower detectors A2, A4, A6, ... A24, B2, B4, ... B24, C2, C4, ... C24.

Further to the preferred embodiment, the radiation sensitive cells of the modules 230 are photodiodes. An array of charge injectors 232 periodically, at the sampling interval, recharges each photodiode of the array to a preselected charge level. As radiation impinges on the photodiodes, the charge is dissipated in proportion to the intensity of radiation and the duration of exposure. At the end of each sampling interval when the injectors 232 recharge each photodiode, the injectors provide a like amount of charge to corresponding cells of a CCD array 234. The CCD array 234 has three rows of cells which in FIG. 9 are labelled with the same designation as the corresponding photodiode of the photodiode array 230. The cells of the CCD array may be arranged in a different order than the corresponding diodes of the photodiode array to accommodate the order of data anticipated by downstream processing equipment. In this manner, the CCD array is loaded with charge values indicative of the amount of charge necessary to recharge each photodiode to the preselected charge, hence, the amount of charge dissipated. Optionally, an indication of the charge remaining on each photodiode may be transferred to the CCD array.

After each sampling, the charge values in each cell rows A, B, and C of the CCD array are shifted rapidly to charge amplifiers 236A, 236B, and 236C, respectively. In the 3 ×24 element array, the charge values are shifted each 1/24th or less of the sampling interval. In this manner, the data from one sampling is converted to serial video signal data and the CCD array is ready to receive new data before the next sampling. If the three rings of detectors are read serially rather than in parallel, the data is clocked out of each row of the CCD array three times as fast, such that all three rows are emptied before the next sampling.

With reference again to FIG. 7, electrical output signals from amplifiers 236A, 236B, and 2360 indicative of the amount of radiation received by the photodiodes of each ring are sampled by a sampling means 240. Buffer memories 242 store the sampled data until a front end processor means 244 digitizes the signals and performs digital signal processing operations, as are known in the art. In the illustrated embodiment, each buffer receives data serially from one of the detector rings. A combining means 246 includes an intraring weighting and filtering means 246a for selectively weighting or filtering the data from the different sized detectors of each ring. Algorithm means 248 converts the data to its logarithmic value. In the illustrated embodiment, three logarithmic circuits each process the data from one detector ring.

The combining means 246 further includes an axial combining means 246b for combining data from the plurality of detector rings. In response to the operator selecting an imaging mode, the combining means selects a corresponding combination algorithm. The selected or combined detector data is reconstructed into an image representation by an image reconstruction means 250 such as a convolution and filtered back projection algorithm. The image representation may be stored in one or more image memories 252 for selective display on one or more video monitors 254. Alternately, the image representations may be stored in computer memory, stored on tape, subject to further processing, or the like.

The operator can select various imaging modes including single and multiple slice modes with different resolutions. In the various modes, the outputs of the detectors are combined in various manners, both axially and transversely or processed independently. For example, in one single slice mode, the outputs of each set of corresponding A, B, and C detectors are combined.

More specifically, the outer collimator adjusts the outer slice width 222 and the inner collimator 224 sets the width of the center slice. The three rings of detectors receive the radiation and produce output signals which could be used to produce three slices. Unless the center and outside detectors are exposed to the same amount of radiation, the three slices have different resolutions. The corresponding elements of the three slices are weighted to accommodate the different resolutions, summed, averaged, or the like. In an embodiment in which the center detectors are three millimeters wide and the outer ones, four millimeters wide, this single slice technique is applicable to single slices with a width of about three to ten millimeters.

In another single slice embodiment, only the center row of radiation detectors are utilized. The adjustable outer collimators or the fixed inner collimators may be utilized to reduce the width of the single slice below the width of the center detector elements.

In a multiple slice mode, three slices are produced. That is, the data from each of the three rings of elements is processed separately. The center slice has the width of the center row of detector elements or the width defined by the inner collimator. The width of the outer slices is separately adjusted by the outer collimator. For many applications, it is advantageous to have all three slices the same width or resolution. In another multiple slice mode, two overlapping slices are produced. Data from corresponding center detector cells and corresponding detector cells on one of the sides are combined to produce one set of data. Data from the same center detector and corresponding detectors of the other outer ring are also combined to produce a second set of data. The two sets of data, which represent overlapping slices, are processed separately. Again, the width of the slices may be adjusted with the collimator 220.

As yet another alternative, transverse combinations of radiation detector elements can be selected. In a spatially weighted view averaging mode, adjacent detector elements within the same one of rings A, B, and C are combined or weighted with elements of different sizes. This effectively averages the views from which the resultant image is reconstructed. In a filtering mode, the data from adjacent detector elements within each ring is time averaged or weighted. In a view averaging mode, the outputs of adjacent detectors are summed or averaged without filtering or weighting. As yet another alternative, the views that are summed or averaged may be the time filtered or spatially weighted views described above. Various other imaging modes or combinations of these imaging modes may, of course, be selected. The logarithm may be taken earlier or later in the processing stream. Preferably, the log is taken before the axial combination to reduce partial volume effects.

Figure 10:
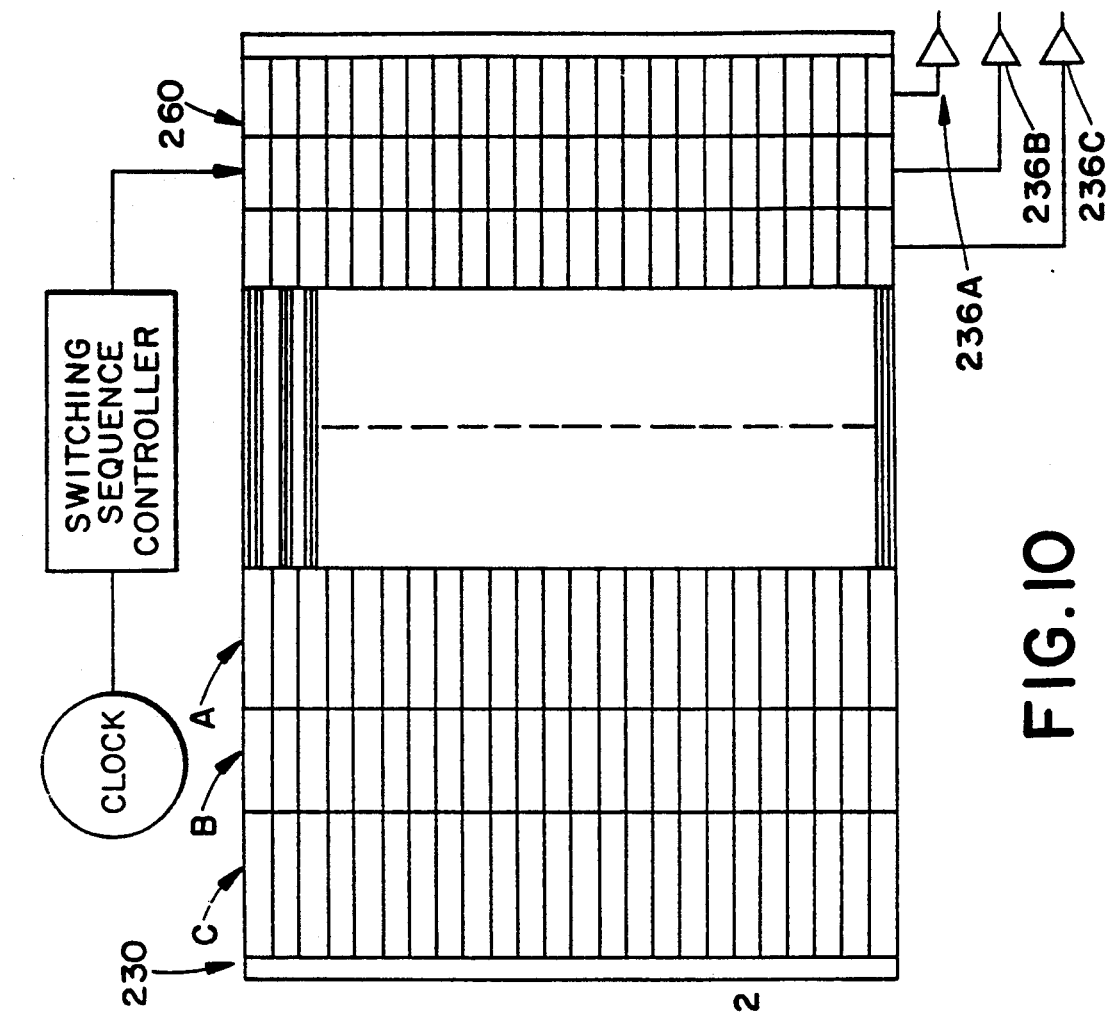

With reference to FIG. 10, in an FET embodiment, the photodiode array 230 is interconnected with an array of FET switches 260. The FETs are each connected with one of the photodiodes for conveying an indication of the conductivity of the sampled photodiode to a corresponding one of output amplifiers 236A, 236B, and 236O. Preferably, an instantaneous voltage across a photodiode and resistor combination is sampled. Optionally, other means besides an FET array or a CCD array may be provided for converting concurrently collected data into serial data signals.

The invention has been described with reference to the preferred embodiment. Obviously, modifications and alterations will occur to others upon reading and understanding the preceding detailed description. It is intended that the invention be construed as including all such alterations and modifications insofar as they come within the scope of the appended claims or the equivalents thereof.

Having thus described the preferred embodiment, the invention is now claimed to be:

1. A method of computed tomographic imaging comprising:
    moving a radiation source and a subject relative to each other so as to irradiate the patient over a plurality of revolutions along a generally spiral path;
    collecting a plurality of views of image data, each view being identifiable by an angular position around the subject and by an axial position along a spiral;
    interpolating at least three views collected at a common angular position around the subject and at at least three displaced axial positions along the spiral over more than two rotations;
    reconstructing the interpolated views into a plurality of image representations corresponding to a plurality of parallel slices through the subject.

2. A method of computed tomographic imaging comprising:
    moving a radiation source and a subject relative to each other so as to irradiate the patient along a generally spiral path;
    collecting a plurality of views of image data, each view being identifiable by an angular position around the subject and by an axial position along a spiral;
    interpolating corresponding views collected over more than two rotations with a cubic weighting function; interpolating with a cubic weighting function;
    reconstructing the interpolated views into a plurality of image representations corresponding to a plurality of parallel slices through the subject.

3. A method of computed tomographic imaging comprising:
    moving a radiation source and a subject relative to each other so as to irradiate the patient along a generally spiral path;
    collecting a plurality of views of image data, each view being identifiable by an angular position around the subject and by an axial position along a spiral;
    interpolating corresponding views collected over more than two rotations with an n-lobe helical weighting function, where n is greater than or equal to 3;
    reconstructing the interpolated views into a plurality of image representation corresponding to a plurality of parallel slices through the subject.

4. The method as set forth in claim 3 wherein views taken at more than four longitudinal positions are interpolated with the n-lobe helical weighting function.

5. The method as set forth in claim 1 wherein the irradiating step includes irradiating the subject with at least two energy levels.

6. The method as set forth in claim 1 wherein the view collecting step includes collecting radiation from the source which has traversed the sample with at least two arcs of radiation detectors, which arcs are displaced longitudinally.

7. The method as set forth in claim 1 wherein the reconstructing step includes reconstructing a plurality of views which span less than or equal to 360° around the spiral.

8. The method as set forth in claim 1 further including moving the subject and radiation source to irradiate the subject along a second spiral path different from the first but covering the same volume.

9. The method as set forth in claim 1 wherein each view represents radiation traveling along one of a plurality of rays extending in a fan-shaped pattern from an apex, each ray being identifiable by an angular position of the view around the spiral and by an angular position of the ray within the fan shaped view; and,
wherein the interpolating step includes interpolating the rays within each view with an interpolating function selected in accordance with both the view angular position and the ray angular position.

10. The method as set forth in claim 1 further including:
monitoring cyclic movement of the subject; and,
synchronizing the relative rotational movement between the subject and the radiation source with the cyclic movement.

11. A method of collecting computerized tomographic image data, the method comprising:
moving a subject and a radiation source such that the subject is irradiated over a first plurality of revolutions along a generally spiral path;
collecting a plurality of views of data each identifiable by its position along a spiral;
interpolating longitudinally corresponding views with an interpolation function;
grouping the interpolated views into a second plurality of groups of views which nominally span less than 360°, the second plurality being larger than the first plurality; and,
reconstructing the second plurality of groups of views into a second plurality of parallel planar image representations corresponding to a second plurality of parallel slices, whereby the views are reconstructed into more planar slices than the plurality of revolutions along the spiral path.

12. A method of collecting computerized tomographic image data, the method comprising:
moving a subject and a radiation source such that the subject is irradiated along a generally spiral path;
collecting a plurality of views of data, each identifiable by its position along a spiral, each view representing radiation traveling along one of a plurality of rays extending in a fan-shaped pattern from an apex, each ray being identifiable by an angular position of the view around the spiral, by an angle of the ray within the view, and by a longitudinal position along the subject;
interpolating corresponding longitudinally displaced rays of different views with a selected interpolating function;
reconstructing groups of views which nominally span other than two adjoining revolutions of the spiral path into a plurality of parallel planar image representations corresponding to a plurality of parallel slices.

13. The method as set forth in claim 11 wherein adjacent groups of views are generated with different energy radiation.

14. The method as set forth in claim 11 further including:
monitoring cyclic movement of the subject; and,
synchronizing relative rotational movement between the subject and the radiation source with the cyclic movement.

15. A method of collecting computerized tomographic image data, the method comprising:
moving a subject and a radiation source such that the subject is irradiated along a generally spiral path;
collecting a plurality of views of data each identifiable by its position along a spiral;
interpolating longitudinally corresponding views with an interpolation function, which interpolation function has a higher band width at selected view angular positions and a smaller band width at other selected view angular positions; and,
reconstructing groups of views which nominally span less than 360° into a plurality of parallel planar image representation corresponding to a plurality of parallel slices.

16. The method as set forth in claim 11 further including moving the subject and radiation source to irradiate the subject along a second spiral path different from the first but covering the same volume.

17. The method as set forth in claim 11 wherein the view collecting step includes collecting radiation from the source which has traversed the sample with at least two arcs of radiation detectors, which arcs are displaced longitudinally.

18. A method of collecting computerized tomographic image, the method comprising:
moving a subject and a radiation source such that the subject is irradiated along a generally spiral path;
collecting a plurality of views of data, each view being defined by a plurality of rays of radiation meeting at an apex with each view being identifiable by an angular position of the apex along a spiral;
filtering rays within the views with each of a multiplicity of filter functions, each filter function being selected in accordance with the angular position of the view and an angular position of the ray within the view;
reconstructing the views into a plurality of parallel image representations.

19. The method as set forth in claim 18 wherein the reconstructing step includes reconstructing groups of views which span about 180° into each planar image representation.

20. A method of generating computerized tomographic image data, the method comprising:
causing relative rotational and longitudinal movement between a subject and a source of radiation such that the subject is irradiated along a generally spiral path, a portion of the subject undergoing cyclic movement relative to other portions of the subject;
converting radiation which has traversed the subject into a plurality of views, each view including a fan shaped array of radiation paths with an apex of each fan shaped array disposed at an identifiable angular position along a spiral around a volume to be imaged;
monitoring the cyclic movement of the subject portion;
controlling relative rotational movement of the radiation source and subject to synchronize the rotational movement and the monitored cyclic movement;

reconstructing the views into a plurality of image representations.

21. A method of generating computerized tomographic image data, the method comprising:
rotating a source of radiation around a subject, an internal portion of the subject undergoing a cyclic event which is independent of the rotation of the radiation source;
converting radiation which has traversed the subject into a plurality of views, each view including a fan shaped array of radiation paths with an apex of each fan shaped array disposed at an identifiable angular position around the subject;
monitoring for the cyclic event in the internal portion of the subject;
controlling a speed of the relative rotational movement of the radiation source to synchronize the source rotation and the monitored cyclic event, whereby the relative rotational movement of radiation source is controlled to be dependent on the monitored cyclic event;
reconstructing the views into at least one image representation.

22. The method as set forth in claim 21 further including operating on a plurality of views, interpolation function to create an interpolated view, and wherein the reconstructing step is performed on the interpolated views.

23. The method as set forth in claim 21 further including alternating an energy output of the source of radiation between at least two levels.

24. The method as set forth in claim 21 wherein the reconstructing step includes reconstructing a plurality of views collected over more than two revolutions around the spiral.

25. A method of computerized tomographic imaging comprising:
rotating a source of radiation around an examination region;
detecting radiation which has traversed the examination region to collect a plurality of views of data, each view being identified by an angular position around the examination region;
filtering each view with one of a plurality of filter functions selected in accordance with the angular position of the view around the examination region;
reconstructing the views into a least one image representation.

26. A method of collecting computerized tomographic image data, the method comprising:
moving a radiation source and a subject relative to each other such that the radiation source radiates the subject generally along a spiral;
simultaneously detecting radiation which has traversed the patient along at least two longitudinally spaced, parallel arcs to concurrently attain views of data lying along at least two interleaved spiral paths;
filtering collected data views;
reconstructing the filtered data views into a plurality of image representations representing parallel displaced planes.

27. The method as set forth in claim 26 wherein each view is defined by a plurality of rays in a fan shaped array and wherein in the filtering step, a filtering is weighted in accordance with an angle of the view around the subject and an angle of the ray within each view.

28. The method as set forth in claim 26 wherein in the irradiating step, an energy of the radiation source beam is varied between at least two energy levels.

29. A method of collecting computerized tomographic image data, the method comprising:
rotating a source of radiation around a subject in an examination region;
moving the source and subject longitudinally relative to each other;
while the source of radiation is rotating, varying an energy of the radiation source between at least two energy levels;
while the energy of the radiation source is varying between the at least two energy levels, detecting radiation which has traversed more than one transverse plane of the subject to collect views of data, each view having an apex at an identifiable angle around and a longitudinal position along the subject and each view including a fan shaped array of radiation beams which have traversed the patient;
filtering the views;
reconstructing the views into at least one image representation.

30. The method as set forth in claim 29 further including a means for advancing the subject through the examination region with a substantially constant velocity.

31. A method of collecting computerized tomographic image data, the method comprising:
rotating a source of radiation around a subject in an examination region;
while the source of radiation is rotating, varying an energy level of the radiation source between at least two energy levels;
detecting radiation which has traversed the subject to collect views of data, each view having an apex at an identifiable view angle around the subject and each view including a fan shaped array of radiation rays which have traversed the patient, each ray having an identifiable ray angle within the fan shaped array;
filtering the views with a filter function;
varying the filter function in accordance with at least one of the view angle and the ray angle;
reconstructing the views into at least one image representation.

32. The method as set forth in claim 29 wherein in the radiation detecting step, views of data are collected which lie along at least two spiral paths around a common imaged volume of the subject.

33. The method as set forth in claim 29 wherein the reconstructing step includes reconstructing a plurality of views which span nominally less than 360° around the spiral.

34. The method as set forth in claim 29 further including monitoring an angular position of the radiation source around the examination region and wherein the energy of the radiation source is varied in accordance with the monitored angular position of the radiation source.

35. A method of generating computerized tomographic data, the method comprising:
rotating a source of radiation around an examination region;
moving a subject through the examination region;

monitoring at least one of (1) the rotation of the radiation source and (2) an energy of the radiation source;

converting radiation which has traversed the subject into a plurality of views, each view including data collected from a fan shaped array of radiation rays with an apex of each array disposed at an identifiable angular position around the examination region;

filtering each view with a filter function;

controlling the filter function in accordance with the monitoring step;

reconstructing the filtered views into at least one image representation.

36. The tomographic imaging apparatus comprising:
a means for moving a radiation source and a subject relative to each other so as to irradiate the subject generally along a spiral;

an arc of radiation detectors for receiving radiation which has traversed the subject;

a means for assembling radiation detected by the radiation detectors into a plurality of views, each view having a plurality of rays emanating from an apex and being identifiable by an angular position of the apex around the subject and an axial position along a spiral path;

an interpolating means for interpolating angularly corresponding rays collected over one of (i) more than two revolutions around the spiral path and (ii) less than two revolutions around the spiral path;

a reconstructing means for reconstructing the interpolated rays into a plurality of image representations;

a memory means for storing the plurality of image representations.

37. A computerized tomographic imaging apparatus comprising:
means for moving a subject and a radiation source such that the subject is irradiated generally along a spiral;

at least an arc of radiation detectors for detecting radiation from the source which has traversed the subject;

a means for assembling detected radiation into a plurality of views, each view having data generated from radiation that traversed the subject along a plurality of rays having an identifiable angular position within a view and each view being identifiable by an angular position around a spiral path and a longitudinal position along the spiral path;

a filtering means for filtering views identified by the same angular position with a filter function;

a reconstructing means for reconstructing groups of views which nominally span 180° into a plurality of image representations;

a memory means for storing the plurality of image representations.

38. A computerized tomographic imaging apparatus comprising:
a source of radiation;

a means for continuously rotating the source of radiation around a subject;

at least an arc of radiation detectors for converting radiation from the source which has traversed the subject into a plurality of views, each view including data converted from a fan shaped array of radiation rays with an apex of each fan shaped array disposed at an identifiable angular position around the subject;

a subject monitoring means for monitoring an internal portion of the subject for an occurrence of a preselected cyclic event;

a controlling means operatively connected to the radiation source rotating means and the monitoring means for controlling relative rotation of the source in accordance with the monitored cyclic event;

a reconstructing means for reconstructing the views into at least one image representation;

a memory means for storing the at least one image representation.

39. A computerized tomographic imaging apparatus comprising:
a subject supporting means for supporting a subject in an examination region;

a radiation source for irradiating a portion of the subject in the examination region with penetrating radiation;

a means for rotating the radiation source around the examination region;

a means for longitudinally advancing the subject supporting means through the examination region at a generally constant velocity;

at least two longitudinally spaced parallel arcs of radiation detectors disposed generally parallel to a path of radiation source rotation for concurrently detecting radiation which has traversed the subject along at least two longitudinally spaced parallel arcs;

a means for assembling the detected radiation into a plurality of views, each view being identifiable by an angular position around the subject and a longitudinal position along at least two interleaved spiral paths around the subject;

a filtering means for filtering the views;

a reconstructing means for reconstructing the filtered views into a plurality of image representations;

a memory means for storing the image representations.

40. A computerized tomographic imaging apparatus comprising:
a source of radiation;

a rotating means for rotating the source of radiation around an examination region;

a radiation source energy control means for controlling an energy output of the radiation source, the radiation source energy controlling means causing the radiation source to vary between at least two energy levels during each revolution around the examination region;

at least an arc of radiation detectors for detecting rays of radiation which have traversed the subject;

a means for assembling detected radiation into a plurality views, each view representing rays meeting at an apex at an identifiable angle around the examination region;

a reconstruction means for reconstructing the views into an image representation.

41. A tomographic imaging apparatus comprising:
a source of radiation;

a radiation source energy control means for controlling an energy of radiation generated by the radiation source;

a means for rotating the radiation around an examination region;

a means for advancing a subject longitudinally through the examination region;

at least an arc of radiation detectors for detecting rays of radiation from the source which has traversed the examination region;

a means for organizing radiation detected by the radiation detectors into a plurality of views, each view representing a fan shaped array of radiation ray with an apex of the array disposed at an identifiable angular position around the examination region;

a filtering means for filtering the views with a filter function;

a monitoring means for monitoring at least one of radiation source rotation and an energy of the radiation source;

a controlling means operatively connected with the monitoring means for controlling at least one of the energy of the radiation source and the filter function;

a reconstructing means for reconstructing the views into image representations;

a memory means for storing the image representations.

42. A computerized tomographic imaging apparatus comprising:

a source of radiation;

a rotating means for rotating the source of radiation around an examination region;

a means for determining an angular position of the source of radiation around the examination region;

at least an arc of radiation detectors for detecting radiation from the radiation source that has traversed the examination region;

means for assembling the detected radiation into a plurality of views, each view being identifiable by an angular position around the examination region;

a filtering means for filtering each view with one of a plurality of filter functions;

a filter function selecting means for selecting among the plurality of filter functions in accordance with the angular position of each view;

a reconstructing means for reconstructing the views into at least one image representation;

a memory means for storing the at least one image representation.

43. A computerized tomographic imaging apparatus comprising:

a source of penetrating radiation;

a means for rotating a source of radiation around an examination region;

a means for advancing a subject through the examination region;

at least an arc of radiation detectors for detecting radiation from the radiation source that has traversed the examination region;

a means for organizing the collected radiation into a plurality of views of data, each view representing a plurality of rays of radiation extending in a fan shaped array from an apex at an identifiable angle around the examination region;

a filtering means for filtering data representing each ray of each view with a filter function selected in accordance with the identifiable angle of the view around the examination region and an angle of each ray within the corresponding view;

a reconstructing means for reconstructing the image representations from the views;

a memory means for storing the image representations.

* * * * *